United States Patent [19]

Hara et al.

[11] Patent Number: 4,908,871
[45] Date of Patent: Mar. 13, 1990

[54] PATTERN INSPECTION SYSTEM

[75] Inventors: Yasuhiko Hara, Machida; Hideaki Doi, Yokohama; Koichi Karasaki, Hadano; Akira Sase, Katsuta, all of Japan

[73] Assignee: Hitachi, Ltd., Tokyo, Japan

[21] Appl. No.: 40,128

[22] Filed: Apr. 20, 1987

[30] Foreign Application Priority Data

Apr. 21, 1986 [JP] Japan .................................. 61-89892

[51] Int. Cl.$^4$ .............................................. G06K 9/00
[52] U.S. Cl. ......................................... 382/8; 382/34; 382/48
[58] Field of Search ........................ 358/101, 106, 107; 356/388, 390, 392–394; 382/1, 8, 9, 10, 30, 34, 41, 44, 45, 47, 48, 49, 55, 56

[56] References Cited

U.S. PATENT DOCUMENTS

| | | | |
|---|---|---|---|
| 4,148,065 | 4/1979 | Nakagawa et al. | 358/101 |
| 4,414,685 | 11/1983 | Sternberg | 382/49 |
| 4,555,798 | 11/1985 | Broadbent, Jr. et al. | 382/8 |
| 4,589,140 | 5/1986 | Bishop et al. | 382/8 |
| 4,654,583 | 3/1987 | Ninomiya et al. | 356/394 |
| 4,692,943 | 9/1987 | Pietzsch et al. | 382/8 |
| 4,729,127 | 3/1988 | Chan et al. | 382/56 |
| 4,748,511 | 5/1988 | Nichols et al. | 382/56 |

FOREIGN PATENT DOCUMENTS

| | | |
|---|---|---|
| 5924361 | 4/1988 | Japan . |
| 58125826 | 4/1988 | Japan . |
| 5242790 | 5/1988 | Japan . |
| 5383768 | 5/1988 | Japan . |

Primary Examiner—Leo H. Boudreau
Assistant Examiner—Jose L. Couso
Attorney, Agent, or Firm—Antonelli, Terry & Wands

[57] ABSTRACT

A printed wiring board circuit-pattern inspection system including a two-dimensionally movable table on which a reference printed wiring board and a printed wiring board to be inspected are placed one after another; an image pickup unit which picks up an image of a circuit-pattern on a printed wiring board by scanning the circuit-pattern in two dimensions, and converting the image into a video signal, a binary pixel forming unit which transforms the video signal into binary pattern data, synchronous signal generator which generates a synchronous signal in synchronism with the scanning operation, a first buffer memory which stores binary pattern data, compressed pattern data memory which stores compressed binary pattern data of a whole reference printed wiring board, data compander which compresses and expands binary pattern, in accordance with the synchronous signal, a second buffer memory which stores, binary pattern data compressed by the data compander and the binary data retrieved from the compressed pattern data memory, and a comparator which compares the reference binary pattern data retrieved from the first buffer memory with the binary pattern data of the board under inspection the synchronous signal thereby providing indication of a defect in the board under inspection.

9 Claims, 5 Drawing Sheets

PATTERN INSPECTION SYSTEM

BACKGROUND OF THE INVENTION

This invention relates to a pattern inspection system and, more particularly, to a circuit-pattern inspection system for automatically detecting broken lines and other visual defects of circuit-patterns on a printed wiring circuit board.

For the inspection of patterns such as circuit-patterns on a printed wiring board, there has been proposed and practiced an inspection method on the basis of comparison between two patterns as described in Japanese Patent Publication No. 59-24361. Another proposal is an inspection system which does not require more than one pattern which is under inspection as described in Japanese Patent Unexamined Publication Nos. 53-83768 and 58-125826. Also for the inspection of a single pattern, there is an inspection method which compares the pattern with its design data as described in Japanese Patent Unexamined Publication No. 52-42790. As a method of inspection based on the memory of an actual pattern, there is a proposal in the bulletin of The Institute of Television Engineers of Japan, Vol. 36, No. 1, pp. 38-44, published in 1982, in which two sets of circuit-patterns on the same printed wiring board are compared, but in this case part of one pattern set is memorized temporarily and another pattern set is compared with it. This is a variation of the method based on the comparison of two sets of actual patterns.

Among these conventional techniques, the method of patent publication No. 59-24361 necessitates two patterns for comparison. The inspection system of patent publication Nos. 53-83768 and 58-125826 cannot detect a defective pattern having a close resemblance to a normal pattern. The method of patent publication No. 52-42790 necessitates an elaborate electric circuit for the generation and development of a pattern from design data, and it is formidable to transfer and store a vast amount of data. The inspection method in the above institute bulletin fails in general applicability even though it is effective for limited uses.

SUMMARY OF THE INVENTION

An object of this invention is to provide a circuit-pattern inspection system for printed wiring boards which facilitates the generation of a reference circuit-pattern to be compared with relatively complex circuit-patterns on printed wiring boards, and also facilitates the comparing inspection even for a single printed wiring board under test.

In order to achieve the above objective, the inventive circuit-pattern inspection system for printed wiring boards includes characteristically a table which mounts a printed wiring board and moves in two-dimensional directions, an image pickup means which operates on the table to move so as to scan a circuit-pattern on the board in two-dimensional directions and produces a video signal from a picked-up image, a binary pixel forming means which transforms the video signal into binary pattern data, a synchronous signal generating means which produces a synchronous signal in synchronism with the scanning operation, a first buffer memory which stores the binary pattern data in divisions correspondingly to regions of the wiring board divided in a direction perpendicular to the scanning direction (X direction), a storage means which stores compressed binary pattern data for the entire printed wiring board, a data companding means which compresses the binary pattern data by eliminating regions of pattern data read out of the first buffer memory, with signals indicative of continuity being left in place of data, when the same pattern data is repeated in the direction (Y direction) perpendicular to the scanning direction, and also expands the compressed pattern data to the original binary pattern, based on the X-Y coordinates provided by the synchronous signal generating means, a second buffer memory which stores the binary pattern data compressed by the data companding means and the binary pattern data retrieved from the storage means for each divided region, and a comparing means which detects a defect of pattern by comparing corresponding portions of the binary pattern data under test provided by a binary pixel data forming means and the binary pattern data provided by the first buffer memory based on the synchronous signal provided by the synchronous signal generating means.

In operation, a printed wiring board under test and a reference printed wiring board are placed on the X-Y stage one after another, the image of circuit-pattern is picked up by the two-dimensional scanning operation of the image pickup means while moving the X-Y stage, binary pattern data is produced by the binary pixel forming means and it is stored in units of region in the first buffer memory, the pattern data retrieved from the first buffer memory is compressed with an MH/MR (Modified Huffman/Modified Relative Element Address Designation) code companding means, the compressed pattern data is stored in units of region in the second buffer memory, the compressed pattern data is read out of the second buffer memory and data for the whole printed wiring board is stored in a storage means such as a semiconductor memory unit, magnetic disk unit or optical disk unit, the pattern data is retrieved from the storage means sequentially for each region and held in the second buffer memory, the compressed pattern data read out of the second buffer memory is expanded with the MH/MR code companding means, the expanded pattern data is held in the first buffer memory, the reference binary pattern data read out of the first buffer memory is compared by the comparing means with binary pattern data of the printed wiring board under test which, subsequently to the reference board, is place on the X-Y stage, imaged by the image pickup means and formed into binary pattern data by the binary pixel forming means, and finally judgment is made as to whether a defect exists in the circuit pattern under test.

The system of the present invention allows the storage means with a relatively small capacity to store a reference binary pattern for a complex printed circuit-pattern including linear and curvilinear components, and enables even a single printed wiring board to be readily inspected through the comparison in the same signal form with the stored reference circuit pattern in synchronism with the formation of the binary pattern data produced by the image pickup means from the board under test.

DESCRIPTION OF THE PREFERRED EMBODIMENTS

Figure 1:
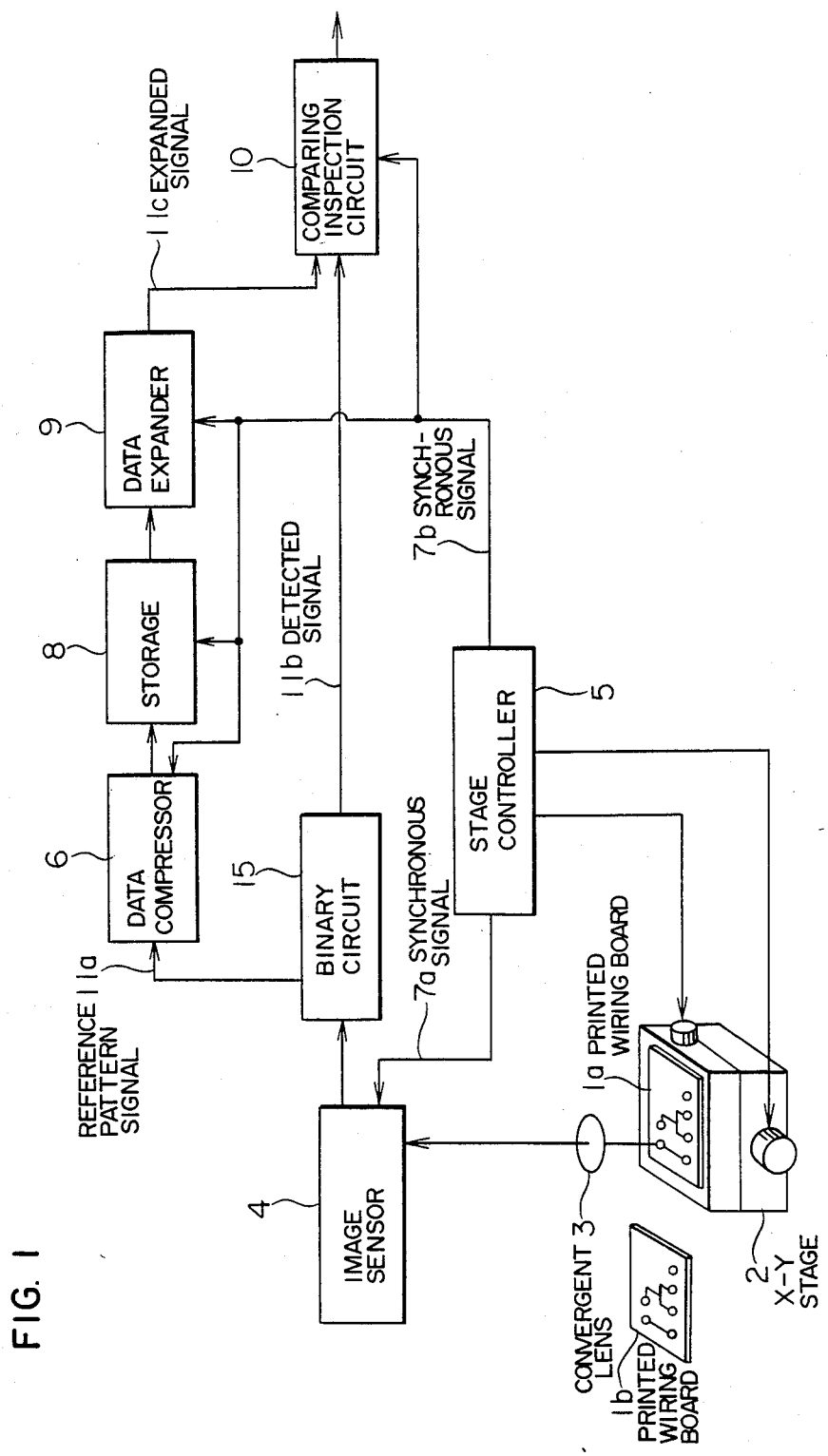
FIG. 1 is a block diagram of the pattern inspection system embodying the present invention.

The inventive pattern inspection system of the present invention employs a means for fast and efficient storing of enormous circuit-pattern data and a means for fast retrieval of the circuit-pattern data and comparing it with an actual circuit-pattern to be inspected. In FIG. 1 showing the arrangement of the inventive inspection system of the present invention, a reference printed wiring board 1a with the formation of a reference circuit-pattern to be memorized is placed on an X-Y stage (table) 2. The circuit-pattern is projected by a convergent lens 3 onto an image sensor 4 (the illumination system is not shown in the figure). The X-Y stage 2 has its position controlled by a stage controller 5 so that a circuit-pattern at an arbitrary position on the board 1a can viewed by the image sensor 4. The image sensor 4 is of the auto-scanning type, such as a television camera or linear image sensor, and its scanning operation is controlled by the synchronizing signal 7a produced by the stage controller 5. The reference image (pattern) signal 11a produced by the image sensor 4 is fed through a binary circuit 15, subjected to data compression in MH system, MR system or M²R system by means of a data compressor 6, and stored in a storage 8. The storage 8 can be a semiconductor memory, magnetic disk, magnetic tape, or optical disk. The optical disk is particularly suited to store a vast amount of circuit-pattern data.

Next, the reference board 1a is replaced with a printed wiring board 1b under test on the X-Y stage 2. In inspecting the board 1b, a circuit-pattern at a specific position is picked up by the image sensor 4 and a produced detected pattern signal 11b is compared by means of a comparing inspection circuit 10 with an expanded reference pattern signal 11c equivalent to the reference pattern signal 11a of the same portion which has been stored. The comparing inspection circuit 10 is described in detail in U.S. Pat. No. 4,148,065.

The reference pattern signal 11a is stored in a compressed form in the storage 8, and therefore it is converted back to the original reference pattern signal by means of a data expander 9 for the sake of comparison with the pattern signal 11b. In order for the data expander 9 to provide pattern data of the same portion as of the detected pattern data 11b, it receives a synchronizing signal 7b from the stage controller 5. The comparing inspection circuit 10 compares the detected pattern signal 11b with the expanded reference pattern signal 11c. By repeating these operations for several normal printed wiring boards generally having normal patterns, it is possible to confirm that pattern data stored in the storage represent normal printed wiring board. Then, the operations are repeated, by using the stored pattern data as a reference pattern data, sequentially for the circuit pattern inspection. In the above system, the data compressor 6 and data expander 9 can be configured as a unitary component.

Figure 3:
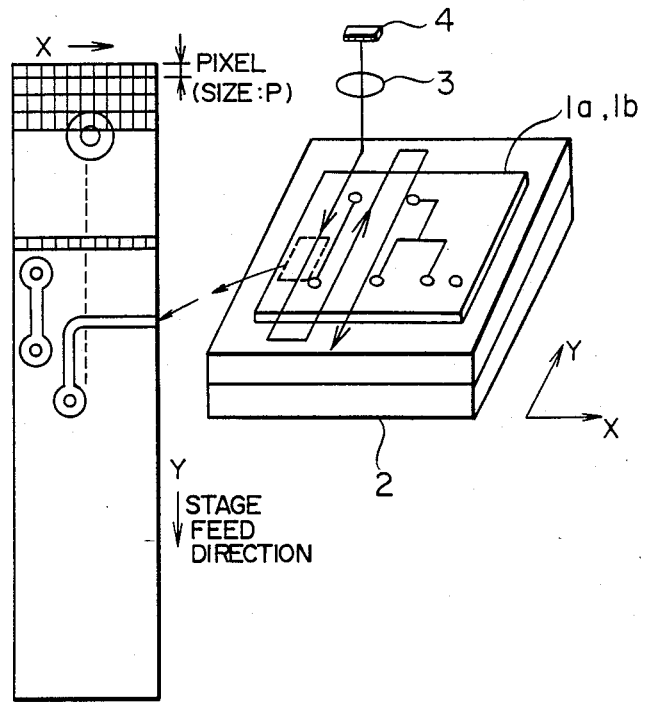
FIG. 3A is a diagram showing a pattern image produced by the two-dimensional scanning of the image pickup means and the binary pixel forming means.
FIG. 3B is a perspective view of the two-dimensional scanning operation.

The following describes the synchronization of the expanded reference pattern signal 11c with the detected pattern signal 11b. The detected pattern signal 11b is produced as a result of bidirectional scanning on the surface of the printed wiring board 1b with the image sensor 4 as shown in FIG. 3B. The image sensor 4 is designed to implement an auto-scanning operation of one line following the advancement of the stage 2 in the Y-direction by 1-pixel interval (dimensioned by a P) in response to the synchronizing signal 7a generated by the stage controller 5. Accordingly, when the image sensor 4 picks up a circuit-pattern and the binary data forming circuit 5 transforms the video signal into a binary pixel data, the image data of the circuit pattern, a part of which is shown in FIG. 3A, is obtained. The image stored in a compressed form has its pixel size (coordinate value) in the Y direction equal to P, and it is stored with a coordinate Y+R retarded by a certain number R of scanning lines, which can be scanned during the time interval corresponding to the process time of the data companding element 12 (i.e., a scanning line coordinate generated by the synchronous signal generating means). In this manner, each pixel is given coordinates, i.e., addresses, in the X and Y directions.

Next, the comparing inspection for the detected pattern signal 11b resulting from the printed wiring board 1b under test with respect to the expanded reference pattern signal 11a derived from the stored image data is carried out as follows. Since the image sensor 4 implements auto-scanning and data expansion in response to the scanning line synchronizing signal 7b which is generated at each advancement of the stage 2 by one pixel interval (P), the two signals 11c and 11b are in complete synchronism. Namely, the storage reads out pattern data which precedes the current scanning line by a certain number R of lines, i.e., on line Y+R-R=Y, and consequently both signals are in synchronism at the comparing means even though time is expended for data compression and expansion.

In entering data of the reference printed wiring board 1a, a positioning mark on the board is used to store pattern data at a specified position, while in positioning the inspection start point on the printed wiring board 1b under test, a positioning mark provided at the same position is used, whereby both printed wiring boards 1a and 1b are brought to complete alignment with each other.

Next, the data compressing, storing and expanding circuits for the reference pattern signal 11a will be described. These circuits are the application of the pattern data companding device (described in Nikkei Electronics, p. 193, published on Jan. 28, 1985) which was first marketed in a recent year.

Figure 2:
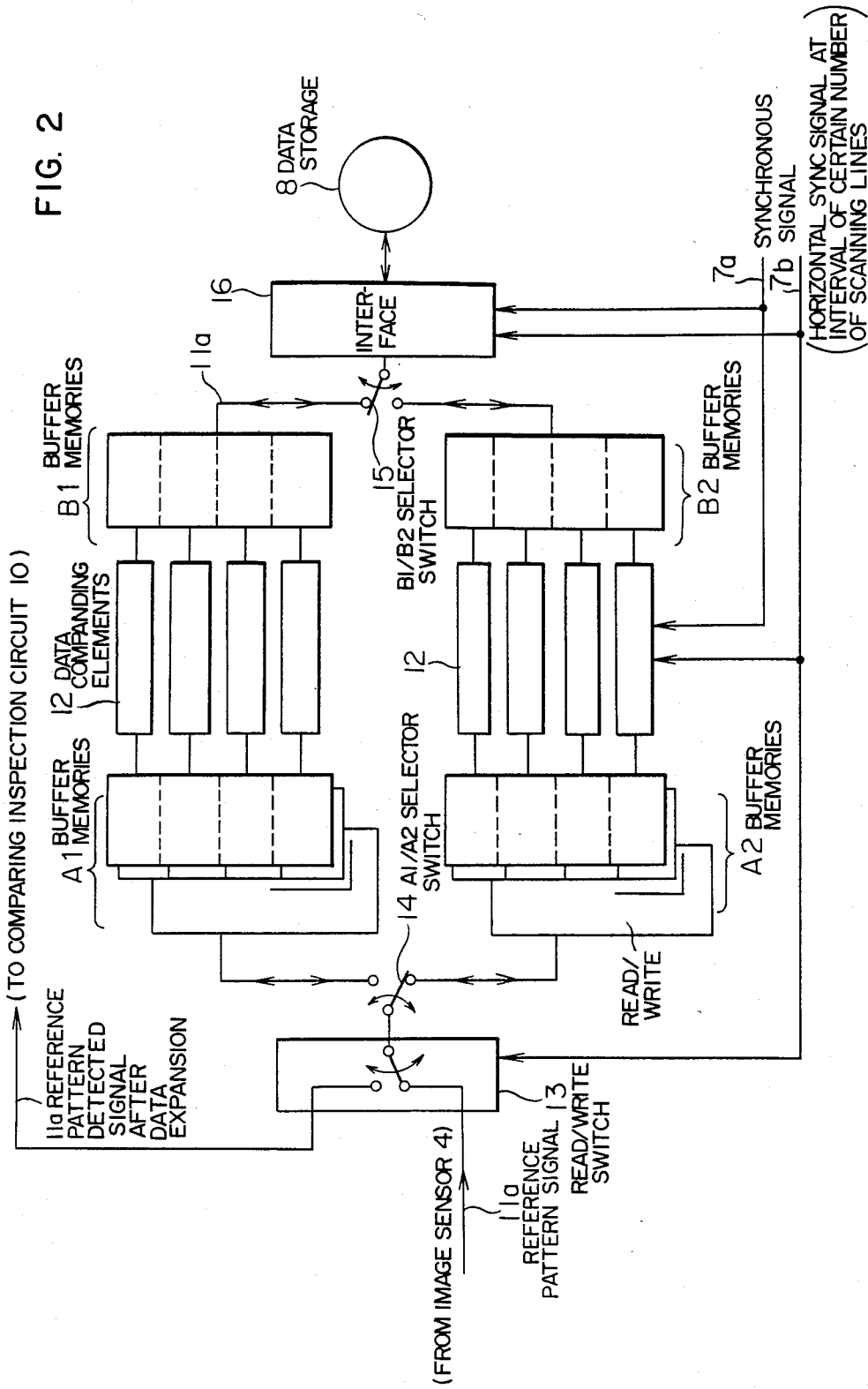
FIG. 2 is a block diagram showing a specific circuit arrangement of the data compressing, storing and expanding blocks in FIG. 1.

As shown in FIG. 2, the reference pattern signal 11a is fed through a read/write switch 13 (the figure shows the switch in write mode) to an A1/A2 selector switch 14. The A1/A2 selector switch 14 sends the reference pattern signal 11a in the form of binary pixel data to a buffer memory A1 (or A2) until it is full, and then switches the signal destination to another buffer memory A2 (or A1). The pattern data stored in the buffer memories A1 and A2 is subjected to data compression by data companding elements 12, as shown in FIG. 5.

Figure 5:
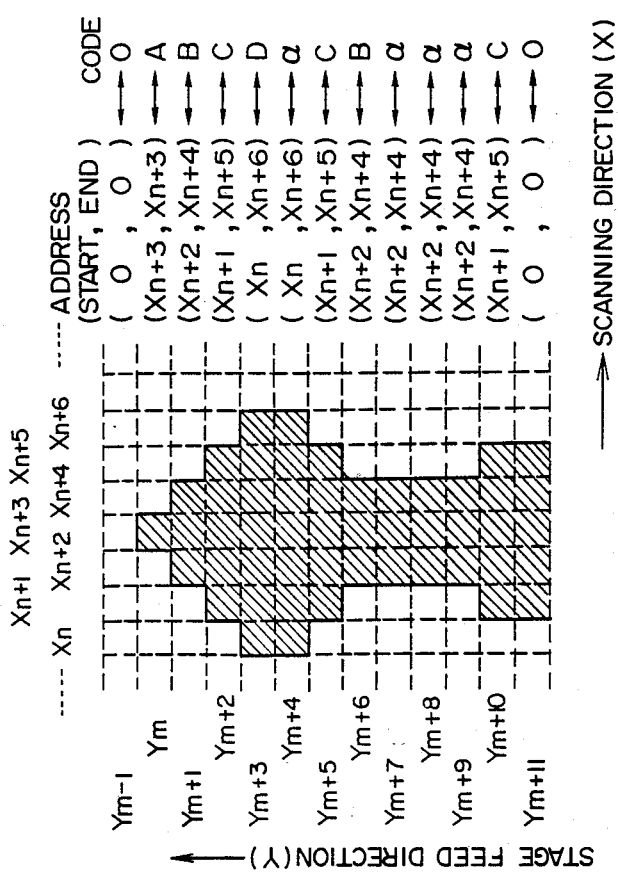
FIG. 5 is a diagram showing the data companding operation by the data companding elements.

FIG. 5 shows on the left-hand side a binary image which has been produced by the binary circuit 15 and stored in the buffer memories A1 and A2. The hatched portion has a logical value of "1" indicating the presence of circuit-pattern, while the blank portion has a logical value of "0" indicating the absence of circuit-pattern.

FIG. 5 also shows at its right-hand side the compressed pattern data. As shown in FIG. 5, no pattern exists in the scanning line $Y_{m-1}$ and hence the compressed pattern data is represented by, for example, "0". In the scanning line $Y_m$, a signal "1" appears at an address $X_{n+3}$ and hence a code A indicative of a start address $X_{n+3}$ and an end address $X_{n+3}$ is obtained from compression of the original data. Next, in the scanning line $Y_{m+1}$, a signal "1" continues from $X_{n+2}$ to $X_{n+4}$ and hence the data is compressed in the X-direction and represented by a code B indicative of a start address $X_{n+2}$ and an end address $X_{n+4}$. In the next scanning line $Y_{m+2}$, a code C, for example, is obtained by similar compression of the pattern data. In the scanning line $Y_{m+3}$, a code D indicative of a start address $X_n$ and an end address $X_{n+6}$ is obtained from compression of the data. The next scanning line $Y_{m+4}$ includes the same pattern as that of the scanning line $Y_{m+3}$ and hence the data of this line is represented by, for example, a code o indicative of "the same as the preceding line". The content of the next line $Y_{m+5}$, which is different from the content of the line $Y_{m+4}$, is represented by the code C indicative of a start address $X_{n+1}$ and an end address $X_{n+5}$ which is the same as the code of the line $Y_{m+2}$. In the next line $Y_{m+6}$, the code B is again produced to indicate a start address $X_{n+2}$ and an end address $X_{n+4}$, which continues from $Y_{m+6}$ to $Y_{m+9}$. Thus, each of the lines $Y_{m+7}$ to $Y_{m+9}$ is represented by the code $\alpha$ as mentioned above. The scanning line $Y_{m+10}$ is represented by the code C indicative of a starting address $X_{n+1}$ and an end address $X_{n+5}$. The lines on and after $Y_{m+11}$, which include no pattern, are each represented by a compressed pattern data "0". In the process of data compression as mentioned above, it is convenient to represent the code $\alpha$ by a shortest binary code, for example "1". Further, the quantity of data after compression can be reduced by representing each of the codes A, B, C . . . by a binary code whose length is determined depending on the frequency in appearance of the corresponding line pattern such that a shorter binary code is used for representing a line pattern which appears more frequently and a longer binary code is used for representing a line pattern which appears less frequently. Incidentally, it should be noted that the line address Y in the Y-direction stored in the memory 8 is represented by the actual address plus R such as $Y_m + R$, $Y_{m+1} + R$, .... The value R is the number of scanning lines necessary for process of data compression and storing, and it is provided by the synchronous signal generating means.

Through the data compression described above, the amount of data of the original pattern signal 11a can be reduced down to about 4%. This data reduction to about 4% is attributable to a large amount of pattern areas that linearly extend along the scanning direction (X direction) and the direction (Y direction) at right angles with the X direction in the case of circuit-patterns on printed wiring boards.

Each data companding element 12 has a maximum processing speed of 5 MHz, and therefore the use of four elements in parallel can achieve data compression for the reference pattern signal 11a received at a maximum data rate of 20 MHz.

Figure 4:
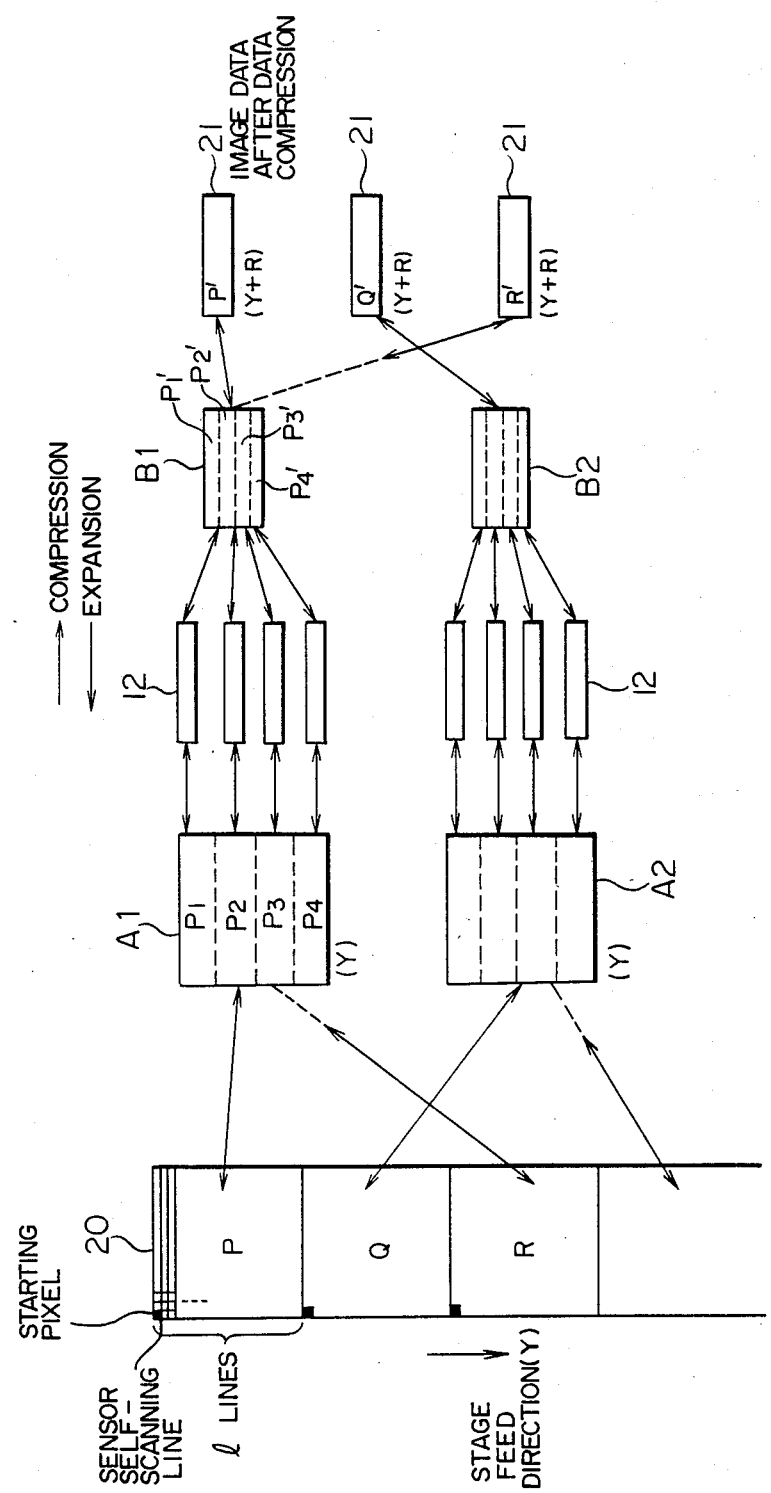
FIG. 4 is a diagram showing data held in the first and second buffer memories in FIG. 2.

The compressed reference binary image data is stored in units of divided regions (P, Q, R and so on) in a buffer memory B1 (or B2) as shown in FIG. 4. A B1/B2 selector switch 15 selects the buffer memories B1 and B2 alternately to transfer the compressed reference binary image data to the storage 8 by way of an interface 16.

In inspecting a printed wiring board 1b, the reference binary image data is retrieved from the storage 8, expanded back to the original reference binary image data 11a by data companding elements 12, and it is stored in the buffer memories A1 and A2. This expanding operation can be accomplished using the data companding elements in a reverse manner thereby taking compressed data and expanding it to its original form. These elements are controlled by the synchronizing signal (a synchronizing signal causing the image sensor 4 to make an auto-scanning following the advancement of the stage 2 by one pixel (P)) provided by the stage controller 5.

Next, the operation of compressing reference image data and storing the result in the storage 8 will be described with reference to FIG. 4.

In a reference pattern image 20, an image P produced as a result of scanning for 1 lines is transferred to the buffer memory A1. This transfer operation corresponds to the entry of reference pattern signal 11a in FIG. 2. The data compressor 12 performs compression for data in the buffer memory A1. In this case, if the stage moves continuously, transfer of the reference pattern signal 11a would continue, but actually the A1/A2 selector switch 14 is operated to the A2 side so that image data Q shown in FIG. 4 is transferred to the buffer memory A2. These operations are repeated and the detected reference pattern image data 20 is compressed continuously without being lost, whereby fast processing is made possible. In this embodiment, the buffer memories A1, A2, B1 and B2 are each divided into four sections so as to achieve parallel processings in data compression from A1 to B1 and data compression from A2 to B2, with the intention of further speedup of operation. Compressed image data 21 is fed through the B1/B2 selector switch 15 and interface 16 and stored in the storage 8.

As will be appreciated from FIG. 4, the reference pattern image data 20 before compression and the image data 21 after compression are in one-to-one correspondence, and therefore if the reference pattern signal 11a and detected signal 11b are in synchronism, the reference pattern 1a and the pattern 1b under test are brought to a complete alignment, allowing the comparing inspection circuit 10 to detect defects through the comparison of both signals.

Although in the above embodiment two sets of buffer memories and data companding devices are used, further speedup of operation is of course possible by the provision of more memories and devices. Conversely, it is also possible for the system to have only one set of buffer memory and data companding device.

It is also possible to operate more data companding elements in parallel, or conversely the number of elements can be reduced to unity.

With the intention of easiness of system construction or enhancement of inspection reliability, it is possible to have the coordinates of the starting pixel 22 in each region (P, Q, R, etc.) (divided into groups of a certain number of lines in the Y direction) of the reference pattern image 20, appended to the compressed data. The coordinates of the starting pixel 22 is available from the stage controller 5 shown in FIG. 1.

According to this embodiment, the reliability of alignment between the reference printed wiring board 1a and the printed wiring board 1b under test is improved. Moreover, the compressed image data 21 has coordinate information for each unit region, and this is effective for readily constructing the function of visual confirmation of pattern shape by expanding the image data.

According to this invention, as described above, the capacity of storage for storing data at a resolution of 10 μm-pixel for a printed wiring board with a 600-by-500 mm size can be reduced to about 15M bytes from the case without data compression which requires a 375M byte capacity.

An optical disk having a capacity of 1.31G bytes on one side can store circuit-pattern data of more than 150 printed wiring boards. If a relatively small number of printed wiring boards needs to be memorized, a semiconductor memory or magnetic tape can be used.

The introduction of the inventive system of the present invention allows prerecording of circuit-pattern data for small-volume variety products, and inspection can be run without waiting for the manufacturing of the printed wiring board to be compared. The inventive system is particularly suitable for the inspection of printed wiring boards in rich-variety, small-volume production. The comparing inspection for circuit-patterns ensures the reliability of inspection. For a volume production of single-type printed wiring board, the first board is used to memorize reference circuit-pattern data, and it can be applied to the inspection of the following products.

We claim:

1. A printed wiring board circuit-pattern inspection system comprising:
    a two-dimensional movable table for mounting thereon a reference printed circuit board and a test printed circuit board to be inspected one after another;
    image pickup means for picking up an image of a circuit board mounted on said movable table, while moving said table so that said image pickup means two-dimensionally scans a predetermined area of said circuit board and for producing a video signal representing the image of the predetermined area of said circuit board;
    binary pixel forming means for transforming the video signal produced by said image pickup means into first binary pattern data;
    data processing means for compressing first binary pattern data of the reference printed circuit board, storing compressed first pattern data and selectively reading out and expanding the compressed first pattern data thereby producing second binary pattern data which is substantially identical to the first binary pattern data of the reference printed circuit board;
    comparing means for comparing first binary pattern data of the test printed circuit board generated by said binary pixel forming means with the second binary pattern data of the reference printed board produced by said data processing means; and
    means including a synchronous signal generator for generating a synchronous signal which is applied to said table, said image pickup means, said binary pixel forming means and said data processing means for controlling operational timing thereof such that said second binary pattern data of the reference printed circuit board produced by said data processing means and said first binary pattern data of the test printed circuit board produced by said binary pixel forming means are applied to said comparing means at the same time wherein said data processing means comprises
    at least two parallel processing sections, each section including
    first buffer memory means having first input/output means and second input/output means for storing said first binary pattern data supplied to said first input/output means from said binary pixel forming means and outputting stored first binary pattern data from said second input/output means and for storing data applied to said second input/output means and outputting stored data from said first input/output means,
    compressing-expanding means having third input/output means connected to said second input/output means and fourth input/output means connected to fifth input/output means of second buffer means for compressing said first binary pattern data applied to said third input/output means, outputting compressed pattern data from said fourth input/output means, expanding data applied to said fourth input/output means and outputting expanded data, as second binary pattern data, from said third input/output means, and
    said second buffer memory means having said fifth input/output means connected to said fourth input/output means and sixth input/output means connected means connected to storage means for storing said compressed binary pattern data applied to said fifth input/output means from said fourth input/output means and outputting stored compressed binary pattern data from said sixth input/output means;
    switching means for applying said binary pattern data part-by-part to said two sections alternately so that said binary pattern data is processed part-by-part parallelly and alternately by said two sections; and
    storage means connected through said switching means to said sixth input/output means of said second buffer memory means of said two sections for storing compressed binary pattern data received from said sixth input/output means of any one of said two sections and supplying stored compressed binary pattern data under control of said synchronous signal to said sixth input/output means of any one of said two sections.

2. A circuit-pattern inspection system according to claim 1, wherein said compressing-expanding means comprises a plurality of data compressing-expanding elements connected in parallel between said first buffer memory means and said second buffer memory means.

3. A circuit-pattern inspection system according to claim 1, wherein the predetermined area of the circuit board is scanned two-dimensionally in X and Y directions perpendicular to each other and said image pickup means comprises a linear image sensor which implements auto-scanning in the X direction while said table is moved for scanning in the Y-direction.

4. A circuit-pattern inspection system according to claim 1, wherein the predetermined area of the circuit board is scanned two-dimensionally in X and Y directions perpendicularly to each other and said image pickup means comprises a linear image sensor which implements auto-scanning in the X direction while said table is moved for scanning in the Y-direction.

5. A circuit-pattern inspection system according to claim 2, wherein the predetermined area of the circuit board is scanned two-dimensionally in X and Y directions perpendicular to each other and said image pickup means comprises a linear image sensor which implements auto-scanning in the X direction while said table is moved for scanning in the y-direction.

6. A circuit-pattern inspection system according to claim 1, wherein the predetermined area of the circuit board is divided into a number of regions and said data processing means includes memory areas for storing coordinates determined for each of said regions.

7. A circuit-pattern inspection system according to claim 1, wherein said first binary pattern data is compressed by said data processing means according to an MH system.

8. A circuit-pattern inspection system according to claim 1, wherein said first binary pattern data is compressed by said data processing means according to an MR system.

9. A circuit-pattern inspection system according to claim 1, wherein said first binary pattern data is compressed by said data processing means according to an MR system.

* * * * *